United States Patent
Kameyama et al.

(10) Patent No.: US 6,420,554 B1
(45) Date of Patent: Jul. 16, 2002

(54) PROCESS FOR PREPARATION OF 3-CEPHEM COMPOUND

(75) Inventors: Yutaka Kameyama; Takae Yamada; Dal Soo Suh, all of Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 09/485,712

(22) PCT Filed: Jun. 30, 1999

(86) PCT No.: PCT/JP99/03540

§ 371 (c)(1),
(2), (4) Date: Feb. 29, 2000

(87) PCT Pub. No.: WO00/01703

PCT Pub. Date: Jan. 13, 2000

(30) Foreign Application Priority Data

Jul. 1, 1998 (JP) .............................. 10-202771

(51) Int. Cl.[7] ...................... C07D 501/04; C07D 501/18
(52) U.S. Cl. ...................... 540/215; 540/226; 540/230; 540/219
(58) Field of Search ................. 540/215, 219, 540/226, 230

(56) References Cited

U.S. PATENT DOCUMENTS

| | | | |
|---|---|---|---|
| 4,252,973 A | 2/1981 | Slusarchyk et al. | ............ 544/21 |
| 5,159,071 A | * 10/1992 | Khanna | ...................... 540/215 |

FOREIGN PATENT DOCUMENTS

| | | |
|---|---|---|
| EP | 0-222-022 A1 | 5/1987 |
| EP | 1-028-118 A1 | 4/1999 |
| JP | 56-25186 | 3/1981 |

OTHER PUBLICATIONS

Lange's Handbook, 12th edition, p. 3–136, 1979.*
Recent Advances in the chemistry of β–Lactam Antibiotics, vol. 38 p. 109 to 124—L. D. Hatfield et al.
S. Torri et al.: "Deprotection of carboxylic esters of beta–lactam homologues", *Journal of Organic Chemistry*, vol. 56, No. 11, 1991:3633–3637.

* cited by examiner

*Primary Examiner*—Mark L. Berch
(74) *Attorney, Agent, or Firm*—Arent Fox Kintner Plotkin & Kahn

(57) ABSTRACT

A process for preparing a 3-cephem compound represented by the formula (3), the process comprising the steps of reacting a β-lactam compound represented by the formula (1) with a phosphorus halide compound in the presence of an organic base to give an imino-β-lactam compound represented by the formula (2), adding a phenol to the same reaction system to cause decomposition due to reaction with an alcohol and simultaneously to remove the protection of carboxylic acid ester, giving a 3-cephem compound represented by the formula (3) or a salt thereof

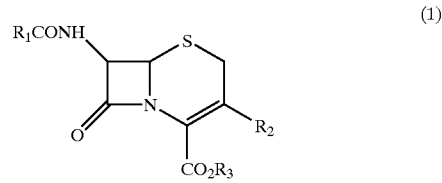

(1)

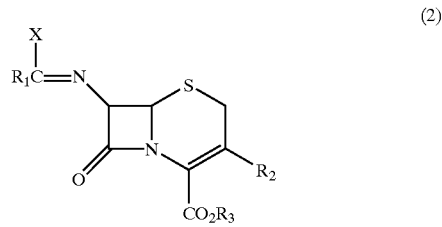

(2)

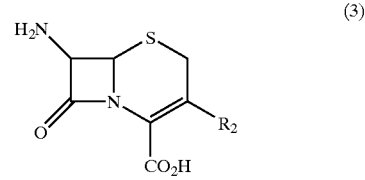

(3)

where $R_1$, $R_2$, $R_3$ and X are as defined above.

8 Claims, No Drawings

PROCESS FOR PREPARATION OF 3-CEPHEM COMPOUND

TECHNICAL FIELD

The cephem compound of the present invention is an important intermediate capable of forming various antibiotics by the introduction of 7-position side chain. For example, a compound of the formula (3) to be described later wherein $R_2$ =vinyl group enables the preparation of cefixime or cefdinir due to a side chain introduced in 7-position. Now these compounds are commercially available as an oral drug (see Katsuji SAKAI, "Handbook of Latest Antibiotics", 9th ed., pp.83 and 86).

BACKGROUND ART

It has been commonly practiced to prepare a 3-cephem derivative of the formula (3) by the substitution of 3-position side chain in 7-aminocephalosporanic acid (7-ACA). However, the process gives only limited compounds having a natural cephalosporin skeleton with 3-position side chain and is infeasible for the preparation of antibiotics having a non-natural cephalosporin skeleton which antibiotics are lately regarded as main antibiotics.

To avert these problems, a compound of the formula (3) was prepared usually according to the process disclosed in L. D. Hatfield et al., Recent advances in the chemistry of β-lactam antibiotics (second international symposium 1980), p.109. The disclosed process comprises reacting a 3-cephem compound of the formula (1) to be described later with a combination of phosphorus halide compound/organic base to give a compound of the formula (2) to be described later, subjecting the compound of the formula (2) to decomposition due to reaction with an alkyl alcohol and to hydrolysis, isolating a compound of the formula (4) or a salt thereof, and removing the protection of carboxylic acid ester of the compound of the formula (4), giving a compound of the formula (3).

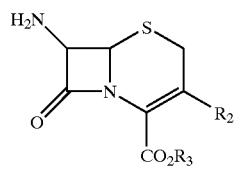

(4)

wherein $R_2$ and $R_3$ are as defined later.

However, the compounds of the formula (4) obtained by the foregoing reaction are mostly unstable and are likely to decompose during isolation and purification. Further, branched aliphatic alcohol has been considered preferable as an alcohol to be used in the decomposition due to reaction with an alcohol because of its reaction mechanism. Yet, the branched aliphatic alcohol is relatively expensive and unsuitable for practical use.

In order to remove the protection of carboxylic acid ester of the compound of the formula (4), it is known to conduct a catalytic reduction using a precious metal catalyst or to treat the compound of the formula (4) with an acid. Known as the latter methods are a method using trifluoroacetic acid [J. Am. Chem. Soc., 91, 5674 (1969)], a method using formic acid [Chem. Pharm. Bull., 30, 4545 (1982)], a method wherein the compound of the formula (4) is reacted with aluminum chloride in the presence of anisole [Tetrahedron Lett., 2793 (1979)] and a method using a phenol [J. Org. Chem., 56, 3633 (1991)].

These conventional methods require the step of isolating the carboxylic acid ester of the formula (4) and the step of removing the protection thereof, namely involve increasing steps. Further, the step of removing the protection poses various problems as described later.

The method involving a catalytic reduction using a precious metal catalyst has a drawback that usually a β-lactam antibiotic has a sulfide linkage in the molecule which linkage poisons the catalyst, resulting in a need to use an expensive precious metal catalyst in a large amount. In addition, the method is not applicable to a β-lactam derivative having, in the same molecule, a group which can be reduced such as a nitro group, carbon-carbon multiple bond or the like. Moreover, the method can not remove, in most cases, such protective groups as a benzyl group which has an electron-donating group as a substituent on a phenyl ring, or a diphenylmethyl group which has an electron-donating group as a substituent on a phenyl ring.

The method using an acid has the following drawbacks. The method using an acid such as trifluoroacetic acid usually requires the use of expensive trifluoroacetic acid in a large amount and would entail a large quantity of loss in recovery and reuse of trifluoroacetic acid after the reaction for the removal of protection. Furthermore, the method gives the desired carboxylic acid compound in a low yield because the β-lactam derivative which is unstable against an acid decomposes during recovery. The method using formic acid necessitates expensive 98–99% formic acid as a solvent in a large excess and gives the desired carboxylic acid compound in a low yield, as is the case with the reaction with trifluoroacetic acid, due to the decomposition of β-lactam derivative which is unstable against an acid during recovery or reuse.

The method using aluminum chloride in the presence of anisole scarcely give the contemplated compound due to the decomposition of β-lactam derivative which is unstable against an acid. As described above, the protection-removing reaction commonly practiced is infeasible in most cases for the compounds of the formula (4) which are mostly unstable. Consequently these conventional processes comprising an isolation step would encounter difficulty in preparing the desired compound in a high yield. Thus, a useful process has not been established yet.

An object of the present invention is to provide a process for preparing a cephem compound of the formula (3) stably and in a high yield without isolating an carboxylic acid ester of the formula (4) which is an unstable intermediate.

DISCLOSURE OF THE INVENTION

According to the present invention, there is provided a process for preparing a 3-cephem compound represented by the formula (3), the process comprising the steps of reacting a β-lactam compound represented by the formula (1) with a phosphorus halide compound in the presence of an organic base to give an imino-β-lactam compound represented by the formula (2), adding a phenol to the same reaction system to cause decomposition due to reaction with an alcohol and simultaneously to remove the protection of carboxylic acid ester, giving a 3-cephem compound represented by the formula (3) or a salt thereof

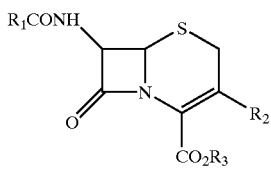

(1)

wherein $R_1$ is arylmethyl group or aryloxymethyl group, $R_2$ is hydrogen atom, halogen atom, hydroxyl group, lower alkoxy group, substituted or unsubstituted lower alkyl group, substituted or unsubstituted lower alkenyl group, lower alkynyl group, heterocyclic thiomethyl group or heterocyclic methyl group, and $R_3$ is benzyl group which may have an electron-donating group as a substituent on a phenyl ring or diphenylmethyl group which may have an electron-donating group as a substituent on a phenyl ring

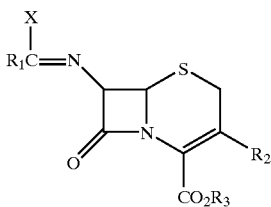

(2)

wherein $R_1$, $R_2$ and $R_3$ are as defined above and X is halogen atom

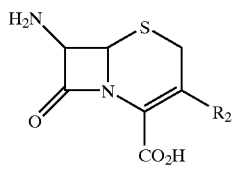

(3)

wherein $R_2$ is as defined above.

According to conventional processes, the compound of the formula (4) which is an unstable intermediate is inevitably isolated, consequently making it difficult to obtain the desired compound in a high yield. Further, it is necessary to use a relatively expensive branched aliphatic alcohol for the decomposition due to reaction with an alcohol. For these reasons, these processes are far from practical. The present inventors found that a phenol is comparable or superior to the conventional branched aliphatic alcohol in the capability of decomposition due to reaction with an alcohol. The inventors also established a reaction system in which a phenol is caused to effectively remove the protection. The inventors successfully conducted a reaction for removal of protection in a stable state without isolating the compound of the formula (4), which has been the problem in the prior art.

Stated more specifically, using a phenol as reagents both for the decomposition due to reaction with an alcohol and for the de-esterification in the series of reactions, the inventors established a process wherein de-esterification reaction is caused to proceed substantially at the same time as the formation of a compound of the formula (4) which is an unstable intermediate in the reaction system, ultimately giving a compound of the formula (3) which is a stable intermediate. In other words, the process obviates, all at once, the problems heretofore raised by the conventional processes.

According to the present invention, there was established a process for preparing a compound of the formula (3) from a compound of the formula (1) wherein the desired compound of the formula (3) can be prepared with a high purity and in a high yield. In the process of the present invention for preparing the compound of the formula (3) from the compound of the formula (1), the reactions can be carried out in a single reaction apparatus, whereby energy-saving and cost-saving benefits are gained to provide one of the features of the present invention.

Examples of the groups mentioned in the specification are as follows unless they are otherwise specified. Exemplary of the halogen atom are fluorine atom, chlorine atom, bromine atom and iodine atom. Examples of lower alkyl group are straight-chain or branched-chain $C_1$–$C_4$ alkyl groups such as methyl, ethyl, n-propyl, isopropyl, n-butyl, isobutyl, sec-butyl and tert-butyl. Exemplary of aryl group are phenyl, anisyl and naphthyl.

Examples of arylmethyl group or aryloxymethyl group represented by $R_1$ are benzyl, tolylmethyl, xylylmethyl, naphthylmethyl, p-methoxybenzyl, p-nitrobenzyl, phenoxymethyl, tolyloxymethyl, p-chlorophenoxymethyl and p-nitrophenoxymethyl.

Examples of $R^2$ groups include known substituents in the 3-position of cephalosporin as disclosed in Mary C. Griffiths, USAN and the USP dictionary of drugs names. More specific examples are hydrogen atom, halogen atom, hydroxyl, lower alkoxy, substituted or unsubstituted lower alkyl, substituted or unsubstituted lower alkenyl group, lower alkynyl, heterocyclic thiomethyl or heterocyclic methyl.

Examples of lower alkoxy group are methoxy, ethoxy and propoxy. Examples of substituted or unsubstituted lower alkyl group are methyl, ethyl, propyl and butyl; chloromethyl, bromomethyl, iodomethyl and like halgenated groups; acetoxymethyl and carbamoyloxymethyl. Examples of substituted or unsubstituted lower alkenyl group are vinyl, propenyl and 2,2-dibromovinyl. Examples of lower alkynyl group are ethynyl and propargyl. Exemplary of heterocyclic thiomethyl group are 1,2,3 triazol-4-ylthiomethyl, 5-methyl-1,3,4-thiadiazol-2-ylthiomethyl, 3-methyl-1,3,4-triazine-5,6-dione-2-thiomethyl, 1-methyltetrazol-5-ylthiomethyl, 1-sulfomethyltetrazol-5-ylthiomethyl, 1-carboxymethyltetrazol-5-ylthiomethyl, 1-(2-dimethylaminoethyl)tetrazol-5-ylthiomethyl, 1,3,4-thiadiazol-5-ylthiomethyl and 1-(2-hydroxyethyl)tetrazol-5-ylthiomethyl. Exemplary of heterocyclic methyl groups are methylpyrrolidinomethyl, pyridiniummethyl, and 1,2,3-triazolemethyl.

Examples of electron-donating group substituted on the phenyl ring of benzyl group or diphenylmethyl group represented by $R_3$ are hydroxy; methyl, ethyl, tert-butyl and like lower alkyl groups; and methoxy, ethoxy and like lower alkoxy groups. The diphenylmethyl group includes a type of the group which is a substituted or unsubstituted phenyl group bonded in the molecule via methylene chain or hetero-atom. Exemplary of benzyl group optionally having an electron-donating group as a substituent on a phenyl ring and diphenylmethyl group optionally having an electron-donating group as a substituent on a phenyl ring are benzyl, p-methoxybenzyl, diphenylmethyl, 3,4,5-trimethoxybenzyl, 3,5-dimethoxy-4-hydroxybenzyl, 2,4,6-trimethylbenzyl, piperonyl, ditolylmethyl, naphthylmethyl and 9-anthryl.

The β-lactam derivative of the formula (1) for use as the starting material in this invention can be prepared by a process comprising preparing a 3-halogenocephem compound by the process disclosed in Torii et al., Tetrahedron Lett., 23, 2187 (1982) and introducing a substituent in the C-3'-position of cephem.

A phosphorus halide compound and an organic base are caused to act on the compound of the formula (1) thus obtained to produce a compound of the formula (2).

Examples of the phosphorus halide compound useful herein are phosphorus pentachloride, phosphorus oxychloride, phosphorus oxybromide and like inorganic phosphorus halide compounds, dichlorotriphenyl phosphite, dibromotriphenyl phosphite, triphenylphosphine dichloride and like organic phosphorus halide compounds.

Exemplary of the organic base to be used are trimethylamine, dimethylethylamine, triethylamine, diisopropylethylamine and like N,N,N-tri(lower alkyl)amines, N-methylpiperidine, N-ethylpiperidine and like N-lower alkylazacycloalkanes, N-methylmorpholine, N-ethylmorpholine and like N-(lower alkyl) azaoxycycloalkanes, N-benzyl-N,N-dimethylamine, N-benzyl-N,N-diethylamine and like N-phenyl(lower alkyl)-N,N-di(lower alkyl)amines, N,N-dimethylaniline and like N,N-dialkyl aromatic amines, pyridine and like nitrogen-containing aromatic amines, diazabicycloundecene, diazabicyclononene and like bicyclic amines and mixtures thereof.

The amounts of the phosphorus halide compound and the base to be used in the reaction are 1 to 10 moles, respectively, per mole of the compound of the formula (1). As required, the phosphorus halide compound and the base may be further added until the compound of the formula (1) is exhausted.

A suitable solvent is used in the series of reactions for the preparation of the compound of the formula (3) from the compound of the formula (1). Examples of useful solvents are dichloromethane, chloroform, dichloroethane, trichloroethane, dibromoethane, propylene dichloride, carbon tetrachloride and like hydrocarbon halides, acetonitrile and like nitriles, diethyl ether, ethyl propyl ether, ethyl butyl ether, dipropyl ether, diisopropyl ether, dibutyl ether, methylcellosolve, dimethoxyethane and like ethers, tetrahydrofuran, dioxane and like cyclic ethers, benzene, toluene, xylene, chlorobenzene, anisole and like substituted or unsubstituted aromatic hydrocarbons, pentane, hexane, heptane, octane, and like hydrocarbons, cyclopentane, cyclohexane, cycloheptane, cyclooctane and like cycloalkanes, methyl formate, ethyl formate, propyl formate, butyl formate, methyl acetate, ethyl acetate, propyl acetate, butyl acetate, methyl propionate, ethyl propionate and like lower alkyl esters of lower carboxylic acids. These solvents can be used either alone or in combination. Preferred solvents are solvent mixtures containing dichloromethane, chloroform, dichloroethane or carbon terachloride as the main solvent.

The amount of the solvent to be used is about 0.5 to about 200 liters, preferably about 1 to about 50 liters, per kilogram of the compound of the formula (1).

The reaction for forming the compound of the formula (2) from the compound of the formula (1) is carried out at a temperature of −50 to 80° C., preferably −30 to 30° C. The reaction time is not limited, but it is sufficient if it continues usually for about 10 minutes to about 3 hours.

Examples of the phenol as reagents both for the decomposition due to reaction with an alcohol and for the removal of protection are phenol, chlorophenol, cresol, methoxyphenol, α-naphthol and β-naphthol. These phenols can be used either alone or in combination. The amount of the phenol to be used is about 0.5 to about 200 kg, preferably about 1 to about 50 kg, per kilogram of the compound of the formula (1).

Since the phenol can be used singly in the above-mentioned reaction, other alcohols need not be used. However, the phenol may be used in combination with aliphatic lower alcohol having 1 to 6 carbon atoms and serving as a co-solvent. Examples of the aliphatic lower alcohol are methanol, ethanol, propanol and like straight-chain lower alcohols, isopropanol, isobutanol and like branched lower alcohols, ethylene glycol, 1,2-propanediol, 1,3-propanediol and like diols. The aliphatic lower alcohol is used in an amount of 0.01 to 0.5 kg per kilogram of the phenol. The reaction for forming the compound of the formula (3) from the compound of the formula (2) is carried out at a temperature of −20 to 80° C., preferably 0 to 50° C. The reaction time is not limited, but it is sufficient if it continues for about 0.5 to about 10 hours.

The foregoing reaction gives the cephem compound of the formula (3) stably in a high yield without isolation of the 3-cephem compound of the formula (4) which is an unstable intermediate.

The compound of the formula (3) can be obtained as a substantially pure product by usual extraction or crystallization after completion of the reaction. The compound (3) can be purified, of course, by other methods.

BEST MODE OF CARRYING OUT THE INVENTION

The present invention will be described in detail with reference to the following Examples to which, however, the present invention is not limited.

EXAMPLE 1

A 43.9 g (1.5 eq.) quantity of a $PCl_5$/pyridine complex was weighed out and placed into a 1-liter 4-necked flask. Then, 250 ml of methylene chloride was added and was cooled to 5° C. Thereto added was 50 g of a compound (1a wherein $R_1=PhCH_2$, $R_2=H$ and $R_3=CHPh_2$), followed by 1-hour stirring. The reaction mixture was cooled to −10° C. or less. Thereafter 200 g of m-cresol was added, followed by 5-hour stirring at 7 to 12° C. Thereto added was 150 ml of cool water after which the mixture was extracted. The organic layer was subjected to extraction with 150 ml of cool water. The obtained aqueous layers were combined and were treated with 2 g of activated carbon. The hydrogen ion concentration was adjusted with 25% ammonia water to a pH of 4, whereby a crystal was separated out. The crystal was collected by filtration and washed with acetone, whereby 18.5 g of the desired compound (3a, $R_2=H$) was obtained (yield 90%).

$^1$H NMR(300 MHz, DMSO-$d_6$/DCl) δ3.60(dd, J=18.9, 5.4 Hz, 1H), 3.66(dd, J=18.9, 3.6 Hz, 1H), 5.11(d, J=5.4 Hz, 1H), 5.16(d, J=5.4 Hz, 1H), 6.53(m, 1H).

EXAMPLE 2

The same reaction as in Example 1 was conducted with the exception of using 32.23 g (1.5 eq.) of $PCl_5$ and 12.5 ml (1.5 eq.) of pyridine in place of 43.9 g (1.5 eq.) of $PCl_5$/pyridine complex, giving 18.7 g of the desired compound (3a, $R_2=H$) (yield 91%). The $^1$H NMR data of the obtained compound (3a) were completely identical with those of the compound obtained in Example 1.

EXAMPLE 3

The same reaction as in Example 1 was conducted except that the mixture obtained after addition of 200 g of m-cresol was stirred at 20 to 25° C. for 3 hours instead of 7 to 12° C.

for 5 hours, giving 18.2 of the desired compound (3a, R$_2$=H) (yield 88%). The $^1$H NMR data of the obtained compound (3a) were completely identical with those of the compound obtained in Example 1.

EXAMPLE 4

The same reaction as in Example 1 was conducted with the of using m-cresol/i-BuOH (200 g/100 g) in lieu of 200 g of m-cresol, giving 19.0 g of the desired compound (3a, R$_2$=H) (yield 92%). The $^1$H NMR data of the obtained compound (3a) were completely identical with those of the compound obtained in Example 1.

EXAMPLES 5 to 12

Table 1 shows the results of carrying out the same reaction as in Example 2 using the under-mentioned solvents including phenols instead of 200 g of m-cresol used in Example 2.

TABLE 1

| Ex. | phenol/alcohol | yield (%) |
|---|---|---|
| 5 | PhOH (200 g) | 89 |
| 6 | m-cresol (200 g)/ethylene glycol (100 g) | 85 |
| 7 | m-cresol (200 g)/1,3-propylene glycol (100 g) | 91 |
| 8 | m-cresol (200 g)/1,2-propylene glycol (100 g) | 90 |
| 9 | PhOH (200 g)/i-BuOH (100 g) | 91 |
| 10 | PhOH (200 g)/ethylene glycol (100 g) | 83 |
| 11 | PhOH (200 g)/1,3-propylene glycol (100 g) | 94 |
| 12 | p-cresol (200 g)/i-BuOH (100 g) | 88 |

The $^1$H NMR data of the compounds (3a) obtained in these examples were completely identical with those of the compound obtained in Example 1.

EXAMPLES 13 to 17

Table 2 shows the results of performing the same reaction as in Example 1 with the exception of using the following solvents in place of methylene chloride.

TABLE 2

| Ex. | Solvent | yield (%) |
|---|---|---|
| 13 | acetonitrile | 90 |
| 14 | tetrahydrofuran | 76 |
| 15 | butyl acetate | 72 |
| 16 | chloroform | 88 |
| 17 | 1,2-dichloroethane | 86 |

The $^1$H NMR data of the compounds (3a) obtained in these examples were completely identical with those of the compound obtained in Example 1.

EXAMPLE 18

The same reaction as in Example 2 was conducted with the exception of using a compound (1b wherein R$_1$=PhCH$_2$, R$_2$=Cl and R$_3$=CHPh$_2$) in place of the compound (1a) and changing the amounts of PCl$_5$ and pyridine to 32.1 g and 12.5 ml, respectively, giving a compound (3b, R$_2$=Cl) (21.0 g, 93%).

$^1$H NMR(300 MHz, DMSO-d$_6$/DCl) δ3.81(d, J=18.0 Hz, 1H), 3.97(d, J=18.0 Hz, 1H), 5.14(d, J=4.8 Hz, 1H), 5.26(d, J=4.8 Hz, 1H).

EXAMPLE 19

The same reaction as in Example 2 was conducted with the exception of using a HI salt of compound (1c wherein R$_1$=PhCH$_2$, R$_2$=vinyl and R$_3$=CH$_2$C$_6$H$_4$OCH$_3$-p) in place of the compound (1a) and changing the amounts of PCl$_5$ and pyridine to 33.6 g and 13.1 ml, respectively, giving a compound (3c, R$_2$=vinyl) (21.1 g, 87%).

$^1$H NMR(300 MHz, DMSO-d$_6$/DCl) δ3.61(d, J=17.1 Hz, 1H), 3.86(d, J=17.1 Hz, 1H), 5.06(d, J=4.8 Hz, 1H), 5.17(d, J=4.8 Hz, 1H), 5.34 (d, J=11.4 Hz, 1H), 5.63(d, J=17.7 Hz, 1H), 6.93(dd, J=11.4, 17.7 Hz, 1H).

EXAMPLE 20

The same reaction as in Example 2 was conducted with the exception of using a compound (1d wherein R$_1$=PhCH$_2$, R$_2$=group (A) below and R$_3$=CH$_2$C$_6$H$_4$OCH$_3$-p) in place of the compound (1a) and changing the amounts of PCl$_5$ and pyridine to 47.4 g and 18.4 ml, respectively, giving a monohydrate of compound (3d, R$_2$=same as above) (21.6 g, 82%).

$^1$H NMR(300 MHz, D$_2$O) δ3.23(d, J=18 Hz, 1H), 3.59(d, J=18 Hz, 1H), 5.08(d, J=4.7 Hz, 1H), 5.19(d, J=4.7 Hz, 1H), 5.25(d, J=14.6 Hz, 1H), 5.55(d, J=14.6 Hz, 1H), 7.95(dd, J=6.0, 8.0 Hz, 2H), 8.44(t, J=8.0 Hz, 1H), 8.81(d, J=6.0 Hz, 2H).

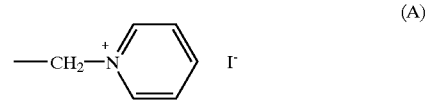

(A)

EXAMPLE 21

The same reaction as in Example 2 was conducted with the exception of using a compound (1e wherein R$_1$=PhCH$_2$, R$_2$=CH$_2$Cl and R$_3$=CH$_2$C$_6$H$_4$OCH$_3$-p) in place of the compound (1a) and changing the amounts of PCl$_5$ and pyridine to 38.5 g and 14.9 ml, respectively, giving a compound (3e, R$_2$=CH2Cl)(19.2 g, 75%).

$^1$H NMR(300 MHz, DMSO-d$_6$/DCl) δ3.63(d, J=18.0 Hz, 1H), 3.72(d, J=18.0 Hz, 1H), 4.51(d, J=11.4 Hz, 1H), 4.58(d, J=11.4 Hz, 1H), 5.14(d, J=5.4 Hz, 1H), 5.21(d, J=5.4 Hz, 1H).

EXAMPLE 22

The same reaction as in Example 2 was conducted with the exception of using a compound (1f wherein R$_1$=PhCH$_2$, R$_2$=group (B) below and R$_3$=CH$_2$C$_6$H$_4$OCH$_3$-p) in place of the compound (1a) and changing the amounts of PCl$_5$ and pyridine to 26.8 g and 10.4 ml, respectively, giving a compound (3f, R$_2$=same as above)(26.9 g, 91%).

$^1$H NMR(300 MHz, D$_2$O) δ2.57(s, 3H), 3.24(d, J=18.0 Hz, 1H), 3.64(d, J=18.0 Hz, 1H), 3.75(d, J=14.1 Hz, 1H), 4.33(d, J=14.1 Hz, 1H), 4.86(d, J=4.8 Hz, 1H), 5.26(d, J=4.8 Hz, 1H).

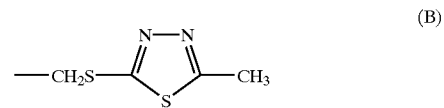

(B)

EXAMPLE 23

The same reaction as in Example 2 was conducted with the exception of using a compound (1g wherein R$_1$=PhCH$_2$, R$_2$=group (C) below and R$_3$=CH$_2$C$_6$H$_4$OCH$_3$-p) in place of the compound (1a) and changing the amounts of PCl$_5$ and pyridine to 27.5 g and 10.7 ml, respectively, giving a sodium salt of compound (3 g, $R_2$=same as above)(28.7 g, 89%).

$^1$H NMR(300 MHz, DMSO-$d_6$) δ3.18(d, J=14 Hz, 1H), 3.64(s, 3H), 3.78(d, J=12 Hz, 1H),3.88(d, J=12 Hz, 1H), 4.58(d, J=4 Hz, 1H), 4.61(s, 1H), 4.70(d, J=14 Hz, 1H), 5.30(d, J=4 Hz, 1H).

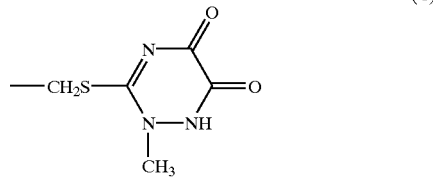

(C)

Reference Example 1

The compounds of the formula (3) prepared in Examples are useful intermediates of cephalosporin antibiotics. For example, using the compound of the formula (3b), cefaclor in wide use as an oral drug can be produced only by introducing a phenylglycyl group in 7-position side chain.

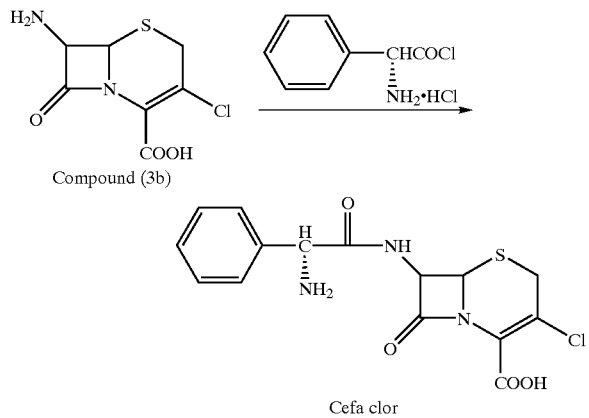

Compound (3b)

Cefaclor

INDUSTRIAL APPLICABILITY

Using a β-lactam compound of the formula (1) as the starting material, a reaction is carried out between the β-lactam compound and a combination of phosphorus halide compound/organic base to produce a compound of the formula (2), the compound of the formula (2) is reacted with a phenol serving as reagents both for the decomposition due to reaction with an alcohol and for the de-esterification reaction, and the protection of carboxylic acid ester is removed simultaneously with the decomposition due to reaction with an alcohol, whereby a compound of the formula (3) or a salt thereof can be isolated and stably produced by a simple procedure with a high purity and in a high yield Further, the process of the present invention can produce a compound of the formula (3) from the compound of the formula (1) using a single reaction apparatus so that energy-saving and cost-saving benefits can be gained.

What is claimed is:

1. A process for preparing a 3-cephem compound represented by formula (3), the process comprising the steps of reacting a β-lactam compound represented by formula (1) with a phosphorus halide compound in the presence of an organic base to produce an imino-β-lactam compound represented by formula (2), adding a phenol to the same reaction system to cause decomposition due to reaction with an alcohol and simultaneously to remove the protection of carboxylic acid ester, producing a 3-cephem compound represented by formula (3) or a salt thereof

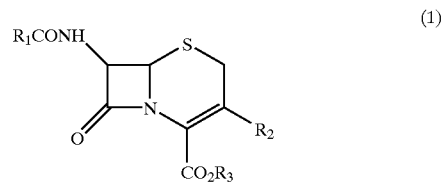

(1)

wherein $R_1$ is an arylmethyl group or an aryloxymethyl group, $R_2$ is a) hydrogen atom, b) halogen atom, c) hydroxyl group, d) lower alkoxy group, e) lower alkyl group or a lower alkyl group substituted with halogen atom, f) lower alkoxyl, g) acetoxy, h) carbamoyloxy, i) lower alkenyl group or a lower alkenyl group substituted with halogen atom, j) lower alkynyl group, k) heterocyclic thiomethyl group selected from the group consisting of 1,2,3-triazol-4-ylthiomethyl, 5-methyl-1,3,4-thiadiazol-2-ylthiomethyl, 3-methyl-1,3,4-triazine-5,6-dione-2-thiomethyl, 1-methyltetrazol-5-ylthiomethyl, 1-sulfomethyltetrazol-5-ylthiomethyl, 1-carboxymethyltetrazol-5-ylthiomethyl, 1-(2-dimethylaminoethyl)tetrazol-5-ylthiomethyl, 1,3,4-thiadiazol-5-ylthiomethyl and 1-(2-hydroxyethyl)tetrazol-5-ylthiomethyl, or l) heterocyclic methyl group selected from the group consisting of methylpyrrolidinomethyl, pyridiniummethyl iodide, and 1,2,3-triazolemethyl, and $R_3$ is a benzyl group which may have an electron-donating group as a substituent on a phenyl ring, or a diphenylmethyl group which may have an electron-donating group as a substituent on a phenyl ring, wherein the electron-donating group is selected from the group consisting of benzyl, p-methoxybenzyl, diphenylmethyl, 3,4,5-trimethoxybenzyl, 3,5-dimethoxy-4-hydroxybenzyl, 2,4,6-trimethylbenzyl, piperonyl, ditolymethyl, naphthylmethyl, and 9-anthryl,

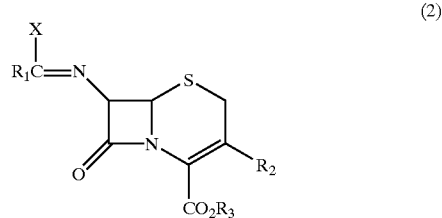

(2)

wherein $R_1$, $R_2$, and $R_3$ are as defined above and X is a halogen atom

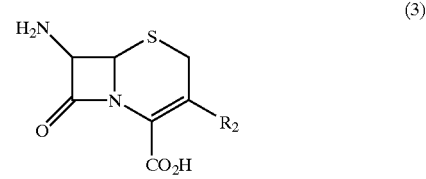

(3)

wherein $R_2$ is as defined above.

2. A process as defined in claim 1 wherein an aliphatic alcohol is used with the phenol in an amount by weight which is less than that of the phenol.

3. A process as defined in claim 2 wherein the aliphatic alcohol is an aliphatic lower alcohol having 1 to 6 carbon atoms or an aliphatic diol having 1 to 6 carbon atoms.

4. A process as defined in claim 1 wherein the phenol compound is phenol, chlorophenol, cresol, methoxyphenol, α-naphthol or β-naphthol.

5. A process as defined in claim 1 wherein the amount of the phenol is 0.5 to 200 kg per kilogram of the compound of the formula (1).

6. A process as defined in claim 1 wherein the amount of the phosphorus halide compound is 1 to 10 moles per mole of the compound of the formula (1).

7. A process as defined in claim 1 wherein the amount of the base is 1 to 10 moles per mole of the compound of the formula (1).

8. A process as defined in claim 2 wherein the aliphatic alcohol is used in an amount of 0.01 to 0.5 kg per kilogram of the phenol.

\* \* \* \* \*